United States Patent [19]

Fromantin

[11] 4,277,497
[45] Jul. 7, 1981

[54] ANALGESIC 2-(M-BENZOYLPHENOXY)-PROPIONIC ACID DERIVATIVES

[75] Inventor: Jean-Pierre M. J. Fromantin, Versailles, France

[73] Assignee: Unicler, Paris, France

[21] Appl. No.: 21,311

[22] Filed: Mar. 16, 1979

[30] Foreign Application Priority Data

Mar. 20, 1978 [FR] France .................. 78 07962

[51] Int. Cl.$^3$ .............. A01N 37/00; C07C 63/37
[52] U.S. Cl. ..................... 424/316; 424/317; 424/308; 562/460; 560/52; 568/333; 260/501.11
[58] Field of Search ............ 562/460; 560/52; 424/317, 316; 260/501.11

[56] References Cited

U.S. PATENT DOCUMENTS

| | | | |
|---|---|---|---|
| 3,398,188 | 8/1968 | Schultz | 562/460 |
| 3,828,093 | 8/1974 | Bays et al. | 562/460 |
| 4,035,376 | 7/1977 | Jansson et al. | 560/52 |
| 4,072,705 | 2/1978 | Mieville | 562/460 |
| 4,153,724 | 5/1979 | Hamazaki et al. | 560/52 |
| 4,162,364 | 7/1979 | Zupančič et al. | 560/52 |

FOREIGN PATENT DOCUMENTS 2321776  3/1977  France ................ 562/460

OTHER PUBLICATIONS

Kawamatsu et al., Chem. Abst., vol. 84, #1644805 (1976).

Primary Examiner—Robert Gerstl
Assistant Examiner—James H. Reamer
Attorney, Agent, or Firm—Wegner & Bretschneider

[57] ABSTRACT

Method of providing an analgesic effect by administring compounds having the general formula I

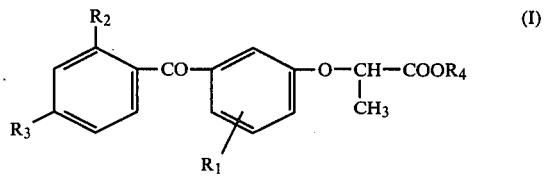

(I)

in which
each of $R_1$ and $R_4$ is independently hydrogen or a $C_{1-4}$ alkyl, and
each of $R_2$ and $R_3$ is independently hydrogen, fluorine, chlorine, bromine or a $C_{1-4}$ alkyl
or their pharmaceutically acceptable salts.

The invention provides also compounds of fromula (I) where each of $R_1$, $R_2$ and $R_3$ is independently hydrogen or $C_{1-4}$ alkyl.

6 Claims, No Drawings

ANALGESIC 2-(M-BENZOYLPHENOXY)-PROPIONIC ACID DERIVATIVES

The present invention relates to 2-(m-benzoylphenoxy)-propionic acid derivatives and their use as analgesics.

The present invention is directed to a method of providing a patient an analgesic effect which comprises administration to said patient of a compound of the general formula (I)

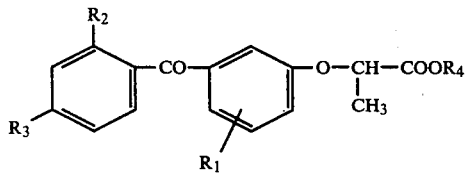

wherein
- each of $R_1$ and $R_4$ is independently hydrogen or a $C_{1-4}$ alkyl group, and
- each of $R_2$ and $R_3$ is independently hydrogen, fluorine, chlorine, bromine or a $C_{1-4}$ alkyl, or a pharmaceutically acceptable salt of the acids.

The invention more particularly relates to the acids of formula I; $R_4=H$ where each of $R_1$, $R_2$ and $R_3$ is independently hydrogen or $C_{1-4}$ alkyl, especially methyl. The compounds are novel and have enhanced activity.

The preferred salts are acid addition salts obtained with organic bases, for example amino acids such as lysine.

The compounds of the formula (I) may be prepared by reacting a 3-hydroxybenzophenone of formula (II)

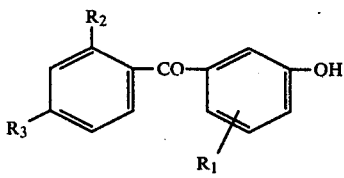

in which $R_1$, $R_2$ and $R_3$ are as defined above, with a α-halogenopropionate of formula III

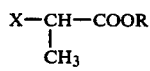

in which X denotes a halogen atom, in particular bromine, and R denotes a lower alkyl group.

The preparation is carried out by heating substantially stoichiometric amounts of the compounds of the formulae (II) and (III) under reflux in an organic solvent such as acetone, and in the presence of an acceptor such as potassium carbonate. The alkyl ester of the acid of formula I may then be hydrolysed into the free acid ($R_4=H$) and purified in the normal way.

The 3-hydroxybenzophenones of formula II are themselves obtained by two different processes, depending on the nature of their substituents.

A. When $R_1$ denotes H, and each of $R_2$ and $R_3$ denotes H or $C_{1-4}$ alkyl, m-methoxybenzoyl chloride is reacted with benzene in the presence of aluminium chloride. Hydrolysis of the 3-methoxybenzophenone obtained then provides the compound of formula II (Ullmann, Ber. 1902, 35, 2811).

B. In the other cases m-nitrobenzoyl chloride, possibly substituted by a methyl group, is reacted with chlorobenzene, bromobenzene, fluorobenzene or m-dichlorobenzene, in the presence of aluminium chloride. A substituted 3-nitrobenzophenone is obtained, which is reduced to the substituted 3-aminobenzophenone. The amine group is then converted into a phenol group by hydrolysis of its diazonium salt. The examples a and b hereinafter illustrate the preparation of 3-hydroxybenzophenones of formula II.

EXAMPLE a

Synthesis of 3-hydroxybenzophenone. ($R_1 = R_2 = R_3 = H$) (II)

0.1 mole of m-methoxybenzoyl chloride and 0.11 mole of aluminium chloride are refluxed for 8 hours in 100 ml of benzene. An oily product is formed, which is distilled (198° C./13 mm Hg). Yield: 60%.

0.1 mole of the 3-methoxybenzophenone thus obtained is heated under reflux for 9 hours in 100 ml of 48% hydrobromic acid. When the hydrolysis is finished the product obtained is recrystallised in a mixture of equal volumes of water and alcohol. Yield: 78%. Melting point of the product obtained: 118° C.

EXAMPLE b

Synthesis of 2-methyl-3-hydroxy-4'-chloro-benzophenone ($R_1=CH_3-2$, $R_2=H$, $R_3=Cl$) (II)

0.5 mole of 2-methyl-3-nitrobenzoyl chloride and 0.52 mole of aluminium chloride are heated for 3 hours between 80° and 100° C. in 80 ml of chlorobenzene. After working up the product obtained in the normal manner, it is recrystallised in ethanol (melting point: 62° C.). Yield: 51%.

150 g (0.7 mole) of stannous chloride, $SnCl_2.2H_2O$, is added in small portions to a suspension of the above nitro derivative (0.25 mole) in ethanol saturated with HCl & cooled to 0° C., and the reaction solution is then allowed to come to room temperature and is heated under reflux for 1 hour. After the mixture has been concentrated, it is taken up in a solution of 20% sodium carbonate, is filtered and the precipitate is extracted several times with chloroform. The amino product is recrystallized in isopropyl oxide, and melts at 70° C. Yield: 88%.

47 g of this amine derivative (0.2 mole) are converted into the diazonium salt at a temperature below 5° C. This salt is then added to 200 ml of a boiling solution of 20% copper sulphate. After cooling, the phenol derivative is extracted with chloroform, is then purified by passing it through animal charcoal in an alkaline medium, and finally the filtrate is acidified.

Yield: 75%. Melting point: 100° C.

The following example illustrates the preparation of compounds of the formula I.

EXAMPLE 0.1 mole of a 3-hydroxybenzophenone of formula II, 0.1 mole of ethyl 2-bromopropionate and 0.1 mole of potassium carbonate are heated under reflux for 10 hours in 250 ml of acetone. After filtering off the precipitated potassium bromide, the acetone solution is concentrated and the oily product thus obtained is distilled. The average yield is 85%.

The ester thus obtained is then hydrolysed at ambient temperature by stirring for 12 hours with an aqueous-alcoholic solution of sodium carbonate. The average yield is 95%.

The table I hereinafter shows, for each compound, the method of preparation A or B of the intermediate benzophenone (formula II), and a physical constant for this intermediate and for the final products (ethyl ester and corresponding acid). The NMR spectrum of each compound confirms that its structure corresponds to the given formula.

The animals are distributed in random batches of 10, but are tested individually. Each test comprises at least two batches:
- a control batch that receives the solvent and phenylbenzoquinone
- a batch treated with the product being investigated.

The investigated products are administered orally, in an amount of 1/10 or 1/40 of the $LD_{50}$, 30 minutes before the injection of the irritant agent. Each mouse then receives 0.25 ml of a 0.02% phenylbenzoquinone solution intraperitoneally.

TABLE I

| Ex.N° | Structural Formulae | Comp.II m.p. | Ester $I_{b.p.}$ | Acid I m.p. |
|---|---|---|---|---|
| 1 | C₆H₅—CO—C₆H₄—O—CH(CH₃)—COOH | (A) 118° C. | 240° C. (13 torr) | 120° C. (≧150° C.)* |
| 2 | C₆H₅—CO—C₆H₃(CH₃)—O—CH(CH₃)—COOH | (A) 123° C. | 208° C. (1.5 torr) | 120° C. |
| 3 | (2,4-Cl₂)C₆H₃—CO—C₆H₄—O—CH(CH₃)—COOH | (B) 135° C. | 190° C. (0.1 torr) | 168° C. |
| 4 | (4-Br)C₆H₄—CO—C₆H₄—O—CH(CH₃)—COOH | (B) 166° C. | 192° C. (0.3 torr) F = 52° C. | 154° C. |
| 5 | (4-F)C₆H₄—CO—C₆H₄—O—CH(CH₃)—COOH | (B) 102° C. | 182° C. (0.8 torr) F = 72° C. | 102° C. |
| 6 | (4-Cl)C₆H₄—CO—C₆H₃(CH₃)—O—CH(CH₃)—COOH | (B) 100° C. | 194° C. (0.3 torr) | 120° C. (218° C.)* |
| 7 | (4-Cl)C₆H₄—CO—C₆H₃(CH₃)—O—CH(CH₃)—COOH | (B) 188° C. | 190° C. (0.3 torr) | 126° C. |
| 8 | (CH₃)C₆H₄—CO—C₆H₄—O—CH(CH₃)—COOH | (A) 122° C. | 206° C. (0.8 torr) | 118° C. (210° C.)* |
| 9 | (2-Cl,4-Cl)C₆H₃—CO—C₆H₃(CH₃)—O—CH(CH₃)—COOH | (B) 98° C. | 214° C. (0.3 torr) | 118° C. |
| 10 | (CH₃)C₆H₄—CO—C₆H₃(CH₃)—O—CH(CH₃)—COOH | (B) 102° C. | 187° C. (0.3 torr) | 90° C. |
| 11 | (CH₃)₂C₆H₃—CO—C₆H₄—O—CH(CH₃)—COOH | (A) 116° C. | 197° C. (0.3 torr) | 120° C. |

*lysine salt

The compounds according to the invention were subjected to pharmacological tests in order to ascertain their therapeutic activity.

They were in particular subjected to the analgesic test of Siegmund, Cadmus and Lu (Proc. Soc. Exp. Biol. Med. 95, 729, 1957) according to which a characteristic painful syndrome is produced in mice by injecting phenylbenzoquinone.

The animals used are Swiss strain mice, weighing 20±2 grams.

The pain syndrome produced by the injection of phenylbenzoquinone causes the animals to stretch their stomach and rear paws, and at the crisis point of the reaction the animal's flanks are very contracted. 5 minutes after the injection of the irritant, the stretching is counted for a period of 10 minutes.

The average number of stretchings is calculated for each batch. The activity of the product under investigations is determined by comparison with the average number of stretchings in the treated animals (N) and the average number of stretchings in the control animals (N').

$$A = \frac{N' - N}{N'} \times 100.$$

The statistical significance of the result thus obtained is evaluated by Fisher's non-parametric test.

The toxicity of the compounds according to the invention administered orally was also determined in mice by Miller and Tainter's method.

The anti-inflammatory activity was measured by the carrageenin oedema test according to Winter and Risley's technique (Proc. Soc. Exp. Biol. 111, 544, 1962). The test was carried out on batches of 10 Wistar strain female rats weighing 180 g, which receives the products in an amount of 1/10 of the $LD_{50}$. The anti-inflammatory activity corresponds to the inhibition of the oedema in the treated batch compared with the control batch.

The results obtained are given in table II below.

TABLE II

| Compound of example N° | $LD_{50}$ toxicity orally (mg/kg) | Analgesic activity at 1/10 of $LD_{50}$ | Analgesic activity at 1/40 of $LD_{50}$ | Anti-inflammatory activity at 1/10 of $LD_{50}$ |
|---|---|---|---|---|
| 1 | 1000 | 86% | 84% | 17% |
| 2 | 750 | 73% | — | 33% |
| 3 | 1500 | 98.5% | 71% | 18% |
| 4 | 1000 | 84% | 58% | 45% |
| 5 | 1500 | 89% | 63% | 26% |
| 6 | 750 | 94% | 83% | 46% |
| 7 | 500 | 81% | — | 21% |
| 8 | 1500 | 84% | 86% | 40% |
| 9 | 750 | 64% | — | |

| Compound of example N°. | $LD_{50}$ toxicity orally (mg/kg) | Analgesic activity at 1/10 of $LD_{50}$ | Analgesic activity at 1/40 of $LD_{50}$ | Anti-inflammatory activity at 1/10 of $LD_{50}$ |
|---|---|---|---|---|
| 10 | 600 | 92% | — | 32% |
| 11 | 2000 | 97% | 31% | 41% |
| Ethyl ester of Example 6 | 1500 | 77% | 73% | 62% |
| Lysine salt of Ex. 1 | 2000 | 97% | 86% | 50% |
| Lysine salt of Ex. 6 | 1000 | 80% | 89% | 57% |
| Lysine salt of Ex. 8 | 2000 | 87% | 36% | 30% |

The compounds of the invention are shown to be valuable analgesics that may be used for example in the treatment of acute and chronic pain; trauma, rheumatic, visceral and neurological pains; toothache, and various other pains such as headache, pain caused by carcinoma, etc.

The compounds may be administered in the conventional pharmaceutical forms, such as tablets, pills, suppositories and injections, in combination with pharmaceutically acceptable excipients and, if necessary, with other active ingredients.

The dosage administered per day for an adult may vary between 5 and 300 mg, preferably 30 to 300 mg orally, or 5 to 50 mg intravenously.

For oral administration, the medicament according to the invention may for example be formulated in one of the following forms:

Tablet

| Compound of Example N° 3 | 50 mg |
| Lactose | 25 mg |
| Icing sugar | 10 mg |
| Starch maize | 25 mg |
| Alginic acid | 15 mg |
| Other excipients, in an amount sufficient to make up | 1 × 200 mg tablet |

Pill

| Compound of Example N° 3 | 50 mg |
| Starch maize | 125 mg |
| Mannitol | 15 mg |
| Alginic acid | 1 mg |
| Sodium alginate | 0.1 mg |
| Talc | 6 mg |
| Glycerol palmitostearate | 3 mg |

The daily dosage may be from 1 to 6 tablets or pills per day.

I claim:

1. A compound having the general formula (I)

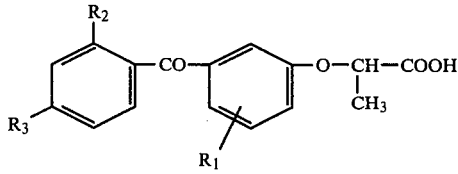

wherein each of $R_1$, $R_2$ and $R_3$ is independently hydrogen or $C_{1-4}$ alkyl, or a pharmaceutically acceptable amino acid salt thereof.

2. A compound according to claim 1 wherein each of $R_1$, $R_2$ and $R_3$ is independently hydrogen or methyl.

3. 2-(3-benzoyl-phenoxy)-propionic acid or its lysine salt.

4. 2-[3-(4-methylbenzoyl)-phenoxy]-propionic acid or its lysine salt.

5. A pharmaceutical composition containing, as active substance, a compound according to claim 1 and a suitable carrier or diluent.

6. The pharmaceutical composition of claim 5 wherein said compound is 2-[3-(4-chlorobenzoyl)-2'-methyl-phenoxy]propionic acid or its lysine salt.

* * * * *